(12) United States Patent
Ward

(10) Patent No.: US 10,822,633 B2
(45) Date of Patent: Nov. 3, 2020

(54) LARGE SURFACE AREA COLLECTION SPONGE FOR CULTURING SAMPLES

(71) Applicant: N. Robert Ward, Bothell, WA (US)

(72) Inventor: N. Robert Ward, Bothell, WA (US)

(73) Assignee: N. Robert Ward, Bothell, WA (US)

( * ) Notice: Subject to any disclaimer, the term of this patent is extended or adjusted under 35 U.S.C. 154(b) by 180 days.

(21) Appl. No.: 15/811,420

(22) Filed: Nov. 13, 2017

(65) Prior Publication Data

US 2019/0144915 A1 May 16, 2019

(51) Int. Cl.
  *C12Q 1/24* (2006.01)
  *C12M 1/30* (2006.01)
  *C12M 1/00* (2006.01)

(52) U.S. Cl.
  CPC ............... *C12Q 1/24* (2013.01); *C12M 23/38* (2013.01); *C12M 33/02* (2013.01)

(58) Field of Classification Search
  CPC ...... C12M 23/10; C12M 23/38; C12M 25/04; C12M 33/02; C12M 33/14
  See application file for complete search history.

(56) References Cited

U.S. PATENT DOCUMENTS

| | | | |
|---|---|---|---|
| 2,835,246 A | 5/1958 | Boettger | |
| 3,684,660 A * | 8/1972 | Kereluk et al. | C12M 41/36 435/305.1 |
| 4,717,667 A * | 1/1988 | Provonchee | C12M 23/04 435/309.4 |
| 5,266,266 A | 11/1993 | Nason | |
| 5,695,988 A * | 12/1997 | Chong | C12M 23/10 435/305.1 |
| 5,905,038 A * | 5/1999 | Parton | B01L 3/0275 422/419 |
| 6,991,898 B2 | 1/2006 | O'Connor | |
| 7,247,273 B2 | 7/2007 | Nunes et al. | |
| 8,075,850 B2 | 12/2011 | Sangha et al. | |
| 8,127,627 B2 | 3/2012 | Ward | |
| 9,027,420 B1 | 5/2015 | Ward | |
| 2004/0042934 A1 | 3/2004 | Nunes et al. | |
| 2005/0084842 A1 | 4/2005 | O'Connor | |
| 2005/0158474 A1* | 7/2005 | Brandt | B05C 17/002 427/401 |
| 2007/0166198 A1 | 7/2007 | Sangha et al. | |

(Continued)

OTHER PUBLICATIONS

Evancho, G.M., et al., "Microbiological Monitoring of the Food Processing Environment," in F.P. Downes et al. (eds.) "Compendium of Methods for the Microbiological Examination of Foods," 4th ed., American Public Heath Association, 2001, pp. 25-30.

(Continued)

*Primary Examiner* — William H. Beisner
(74) *Attorney, Agent, or Firm* — Christensen O'Connor Johnson Kindness PLLC

(57) ABSTRACT

A sampling device and a method for taking samples. The sampling device includes a cap having two ends and a collection sponge attached on one end, wherein a collection sponge diameter is greater than a collection sponge height. A lid is removably attached to a first end of the cap to cover the collection sponge; and a bowl is removably attached to a second and opposite end of the cap. The bowl can contain an enrichment broth.

20 Claims, 5 Drawing Sheets

(56) References Cited

U.S. PATENT DOCUMENTS

2011/0004122 A1     1/2011   Sangha
2013/0177938 A1     7/2013   Ward

OTHER PUBLICATIONS

Wiczer, J., and K.B. Lee, "A Unifying Standard for Interfacing Transducers to Networks—IEEE-1451.0," presented at ISA Expo 2005: Automation + Control, Jan. 1, 2005, Research Triangle, N.C., 10 pages.

\* cited by examiner

LARGE SURFACE AREA COLLECTION SPONGE FOR CULTURING SAMPLES

BACKGROUND

Sampling of surfaces is routinely done by companies to control the type and level of microorganisms in their production environment. For example, many food companies perform surface sampling in an effort to reduce the possibility of pathogens (disease-causing organisms) and/or spoilage organisms entering food products during production from environmental sources. *The Compendium of Methods for the Microbiological Examination of Foods* ($4^{th}$ edition), pp. 25-30, discusses the rationale for environmental sampling, strategies for collecting a sample, and commonly used methods for collecting a sample. Another system is described in U.S. Pat. No. 5,266,266.

SUMMARY

In an embodiment, a sampling device in accordance with the present invention has a large area collection sponge affixed to a raised flat surface of a cap with two threaded sides, one of which is a collection sponge side with an attached lid to protect the collection sponge prior to use and an opposing side from the collection sponge for attaching a bowl containing an enrichment broth. Right before sampling a surface, the lid over the collection sponge is removed to expose the collection sponge with the user grasping the bowl. The bowl functions as a large grasping surface to allow the user to vigorously scrub the surface while minimizing the possibility that the user's hand will accidentally contaminate the surface of the collection sponge during sampling. Once the sample is collected, the bowl containing the enrichment broth is removed from the cap and the re-attached to the opposing side so as to expose the collection sponge to the enrichment broth. The bowl that was originally above the collection sponge is reattached to the side opposite of the collection sponge.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
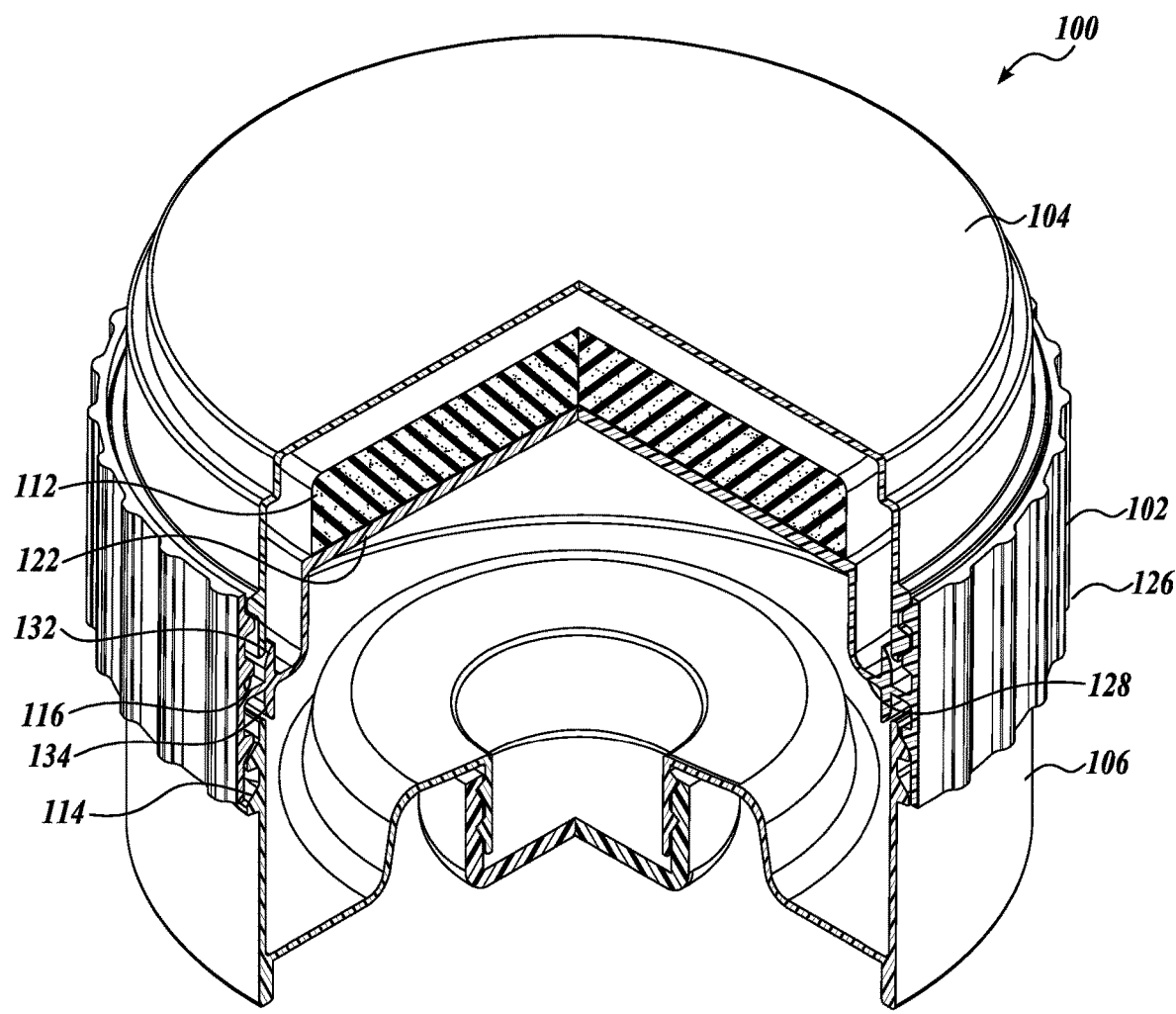
FIG. 1 is a diagrammatical illustration of an embodiment of a sampling device and a quarter section showing the internal construction.

Microorganisms residing on a surface may be firmly attached to that surface or part of a matrix of cells and extracellular materials, commonly referred to as a biofilm, that adhere strongly to a surface. To get an accurate determination of the presence and/or the level of microorganisms on the surface, aggressive scrubbing of the surface is critical to lift the strongly attached cells. This means that the material of the sampling device that contacts the surface must be sufficiently robust to withstand vigorous scrubbing, even if the surface is rough. Moreover, the material contacting the surface must be non-toxic (that is, will not adversely affect the survival or culturing of microorganisms after sampling) and without chemical contaminants that might interfere with a diagnostic test once the sample is brought to the laboratory.

Food industry has used various devices for collecting surface samples depending upon the nature of the surface to be tested. For example, small, hard-to-reach areas are often sampled using a traditional clinical style swab with a shaft and a fiber tip, such as rayon or cotton. A fiber tip swab however can unravel during sampling, especially when sampling a rough surface. Moreover, while the thin and bendable shaft of this type of swab is helpful for reaching into a tight area (a notable benefit for collecting a clinical specimen where delicate tissues are sampled), it is an inadequate tool when attempting to dislodge microorganisms that are part of a biofilm community.

Recently, the food industry has adopted the World Bioproducts' PUR-Blue Sampler built with a rigid plastic shaft and a polyurethane foam tip that allows the user to aggressively press the foam to the surface without concern with the foam tip disintegrating. These sampling devices are useful for sampling "nooks and crannies" and areas up to about 1 square foot, although sampling efficiency and possibly effectiveness wane as sampling areas approach or exceed 1 square foot.

Sampling of areas of 1 square foot or greater has historically been accomplished using sponges of a size of about 1.5 inches by 3 inches that are either held directly by the user wearing a sterile glove or mounted onto a handle that allows the user to collect the sample without contacting the sponge (for example, U.S. Pat. No. 8,127,627 B2). These sponge sampling products are commercially available dry or pre-hydrated with a collection broth. World Bioproducts LLC offers sampling devices utilizing both cellulose sponges and polyurethane sponges, with and without a handle for sample collection. A dry sponge is sometimes used to sample a surface that is wet or the user may add a preferred collection broth to the sponge prior to surface sampling. These sponge sampling devices are typically packaged in a flexible sample bag with a wire closure that preserves the sterility of the sampling sponge prior to use and acts as a transport container for the sponge after the sample is collected. The disadvantages of these sample bags are that they are bulky, can be difficult to manipulate without accidentally introducing contaminants, and may leak during transportation back to the laboratory.

Many surface samples collected in food processing facilities are shipped by overnight carriers to remote laboratories, such as a central corporate laboratory or an independent contract laboratory, using coolers with frozen blue ice packs to maintain a temperature of 4° C. to 8° C. during transport. The time from sample collection to processing in the laboratory may be up to 48 hours, and sometimes 72 hours when sample collection and transit occurs over a weekend.

The microbiologist collecting the sample needs to be aware that organisms present on a surface to be sampled may be in an injured state caused by application of a sanitizer, or because they reside in a nutrient depleted and/or dry environment. These stressed organisms could die if not properly handled when and after the sample is collected. It should be noted that even though the microorganisms are in a stressed state, these organisms, if introduced from the environment into a food product, might recover from injury and begin to grow, resulting in a danger to the consumer.

Another key to successfully collecting, transporting, and processing a sample from a surface is the solution used to hydrate the sponge or swab. The ideal solution for collecting a sample ("collection broth" or "collection solution") is one that can neutralize residual sanitizer that may be present on the surface and picked up during sampling, can support the viability of injured organisms collected by the collection sponge or sponge until the sample is processed in the laboratory, and is non-toxic so that if it is left on the sampled surface (perhaps a food contact surface) there will not be harmful consequences to the consumer if this material comes in contact with the food. For example, it would be best to utilize a collection solution that is capable of neutralizing all types of commonly used sanitizers (including quaternary ammonium, phenolic, chlorine, and peracetic acid sanitizers), would provide an environment that has a neutral pH and can maintain osmotic balance, would supply a nutrient(s) that can aid the injured cells in their recovery and is not dangerous to the consumer. A collection solution that is not dangerous to the consumer is one that does not contain allergens, antibiotics, heavy metals and metal salts, and potentially toxic and/or cancer causing substances. World Bioproducts offers sampling devices with its proprietary HiCap Neutralizing Broth which embodies the attributes of an ideal collection solution (www.worldbioproducts.com). Representative collection broths or solutions are disclosed in U.S. Application Publication No. 2013/0177938 (application Ser. No. 13/735,798, filed on Jan. 7, 2013), incorporated herein expressly by reference for all purposes, and in particular, for the teaching of collection broths and solutions for use in the present sampling device.

A presence/absence test is one that is run for the purpose of determining whether a pathogen (for example, *Listeria monocytogenes*, *E. coli*, or *Salmonella*) or spoilage organism (for example, *Pseudomonas* spp.) is present in the sample. To conduct a presence/absence test, an enrichment broth is added to the sampling device upon receipt in the laboratory. The enrichment broth has three purposes. The first is to help a potentially injured pathogenic cell to recover from its injury so that it can initiate growth. The second purpose is to support the growth of the pathogen so that it reaches a high level for detection. The third purpose is to completely inhibit or slow the growth of microorganisms ("competitor" organisms) that may compete for nutrients in the enrichment broth and interfere with the detection test. The ideal enrichment broth is one that optimizes recovery of highly injured organisms, supports their unrestricted growth, and totally suppresses the growth of competitor organisms. Sometimes it is not necessary to suppress the growth of competitor organisms and a non-inhibitory enrichment (also referred to as a non-selective enrichment broth) is used, if the diagnostic test has sufficient sensitivity and specificity so that low levels of the pathogen can be detected in the presence of high concentrations of competitor organisms.

If a sponge in the sample bag was received by the laboratory, typically 40 to 100 milliliters of enrichment broth are added directly to the bag. As an example, if the laboratory desires to determine if Listeria monocytogenes was present on the sponge, 40 to 100 milliliters of a broth formulated to encourage greater growth of L. monocytogenes over other non-Listeria microorganisms (for example, Demi-Fraser Broth), would be added to the sample bag. The sponge and broth would then typically be incubated for 20 to 24 hours before a diagnostic test is run.

Below is a table showing some commonly used enrichment broths for growing pathogenic microorganisms that are important to food industry. The United States Food and Drug Administration's *Bacteriological Analytical Manual* (BAM) (www.fda.gov) is a source for information on the enrichment of samples for pathogens, as well as the *Compendium of Methods for the Microbiological Examination of Foods* (4$^{th}$ edition). Enrichment broths for pathogenic microorganisms continue to change and a recent article by Stromberg et al (*Current Microbiology*, 2015, 71:214-219) concerning the enrichment of pathogenic *E. coli*, illustrates this point. These investigators compared different enrichment broths with non-selective or selective properties for the recovery of pathogenic strains of *E. coli*.

TABLE 1

Some enrichment broths used to culture pathogenic microorganisms important to food industry

| Pathogen Tested For: | Type of Enrichment Broth | Selective Agents Added to the Broth to Inhibit Competitor Microorganisms | Potential Hazards Associated with the Selective Agent(s) in These Broths |
|---|---|---|---|
| *Listeria* spp., including *L. monocytogenes* | UVM Modified *Listeria* Enrichment Broth | Nalidixic Acid; Acriflavine | Nalidixic acid has potential to cause convulsions and hyperglycemia; Acriflavine may cause birth defects |
| | Paradigm Diagnostics *Listeria* Indicator Broth | Nitrofurantoin: Cycloheximide; Naldixic Acid; Ceftazidime; Phosphomycin; Polymyxin E | Nitrofurantoin is toxic to kidneys and nervous system; Cycloheximide is a suspected teratogen; Ceftazidime, phosphomycin, and polymyxin E may cause allergic reaction |
| | Demi Fraser Broth | Nalidixic Acid; Acriflavine; Lithium Chloride | Lithium chloride is a possible teratogen; is mutagenic |

TABLE 1-continued

Some enrichment broths used to culture pathogenic microorganisms important to food industry

| Pathogen Tested For: | Type of Enrichment Broth | Selective Agents Added to the Broth to Inhibit Competitor Microorganisms | Potential Hazards Associated with the Selective Agent(s) in These Broths |
|---|---|---|---|
| | Universal Pre-enrichment | None (non-selective broth) | |
| | Listeria Enrichment Broth | Cycloheximide; Acriflavine; Nalidixic Acid | See Above |
| Salmonella spp. | Buffered Peptone Water | None (non-selective broth) | |
| | Universal Pre-enrichment | None (non-selective broth) | |
| Pathogenic Strains of Escherichia coli | Buffered Peptone Water, Tryptone Phosphate Broth or Brain Heart Infusion Broth, E. coli (EC) Broth | None (non-selective broth) | |
| | TSB-NVRBT | Novobiocin, Vancomycin, Rifampicin, Bile Salts, Potassium Tellurite | Novobiocin may cause irritation to eyes, skin, and membranes; vancomycin may cause allergic reactions; rifampicin is hepatotoxic |
| | Universal Pre-enrichment | None (non-selective broth) | |

A new surface sampling device that allows the user to collect the sample and begin enrichment immediately or soon after sample collection was described in U.S. Pat. No. 9,027,420 B1. This device uses a cap with two threaded sides. On one side, a shaft with a collection sponge extends from the cap. The swab of this first side is enclosed with a watertight tube. A second tube is coupled to the second side of the cap and can contain an enrichment broth. Following collection of a surface sample with the swab by removing the first tube from the cap, the swab can be immediately placed in the enrichment broth by unthreading the second tube from the cap, immersing the swab into the enrichment broth and threading this second tube into the cap to produce a watertight fit. A commercial product called PUR-Blue DUO that encompasses the art described in this patent is available from World Bioproducts (www.worldbioproducts.com). The device described in U.S. Pat. No. 9,027,420 B1 has obvious advantages over the challenges of traditional sampling, transport, and culturing in the laboratory. One key advantage is that the surface sample can be enriched immediately after collection. Moreover, there is the obvious advantage of convenience, whereby the enrichment step is initiated at the point of sample collection and the need to perform this processing step is eliminated when the sample arrives in the laboratory. While the device of U.S. Pat. No. 9,027,420 B1 offers important advancements for the sampling and culturing of microorganisms collected by the device during sampling, it has limitations that the current application effectively circumvents. The present disclosure is related to a sampling device 100 (as will be described herein with reference to the FIGURES) for collecting samples from a large surface area that may extend in area to one square foot or more, for example. However, the surface area is not meant to be limiting.

As compared to the traditional practices described above for collection, transport, and enrichment only when the sample arrives in a laboratory, an embodiment of the present invention provides a system for detecting a pathogen in an environmental sample in a way that allows the analyst to initiate enrichment of the sample immediately after sample collection. The device 100 in accordance with an embodiment of the invention provides a rapid initiation of the enrichment process. Accordingly, there will be an increased likelihood that the injured organism will be recovered and detected. In the device 100, the collection sponge can be placed immediately into the enrichment broth after sample collection. A second benefit of starting the enrichment step right after sample collection is that the target organism may be detected earlier since the test is started earlier. In this case, it may not be desirable to transport the sample in a cold environment (as it typically done with a "blue ice" pack added to the transportation container). Rather, growth may be initiated by incubation at ambient temperatures while the processed sample is brought to the laboratory, and then placed in an incubator at temperatures of 30° C. or 35° C. to complete incubation. A further option is to place the sampling device 100 into a special transportation incubator that allows the sampling device 100 to be held at an optimal growth temperature during the transportation period.

Consequently, when the sampling device 100 arrives in the laboratory, incubation is completed, or mostly complete, and the detection assay can be started for the target organism without the need for further, or at least full, incubation. A third benefit of starting the sample enrichment step immediately is convenience. This eliminates the need for further handling in the laboratory to initiate the enrichment process.

In some instances, the collection solution of the sampling device 100 can be the same as the enrichment solution. In most cases, this is not possible or desirable as the sample collection broth needs to be free of toxic materials so that it can safely be used on product contact surfaces. Many enrichment broths contain components such as antibiotics or other materials that may be toxic to humans if ingested (see Table 1). Also, food industry typically employs collection solutions that contain sanitizer neutralizing properties, anticipating that sanitizer residues may be present on the surface when the sample is taken. Sanitizers that are picked up by the collection device and not neutralized could result in false negative results if they kill microorganisms collected by the sampling device prior to testing in the laboratory.

In an embodiment, the device 100 can be provided with an enrichment broth supplied by the manufacturer or the user could add their desired broth to the device 100 just before sample collection. In an embodiment, the user has the capability to perform tests for different types of bacteria (for example *Listeria, Salmonella* and/or *E. coli*) from a single sampling device 100. Universal Pre-enrichment Broth has been used for enriching a sample for *Listeria, Salmonella* and *E. coli* prior to running a diagnostic test and this broth could be added to the bowl of the device 100 by the manufacturer or by the laboratory prior to sample collection.

In situations where a sample is taken in a production environment, it can be advantageous that all components of a sampling device that are brought into the production area are accounted for and carried out after sample collection is completed. The reputation of a company, for example, would be adversely impacted if a user collecting a sample accidentally lost track of a component of the sampling device, the part accidently was introduced into the product being manufactured, and a consumer encountered this part when consuming the product, such as a food or pharmaceutical. For example, when a user employs a sponge sampling device in a flexible sample bag with wire closure, it is necessary to tear away the top of the bag to gain access to the sampling sponge or handle. The piece of the sampling bag once removed must be carefully accounted for and secured so that it is removed from the production environment when sample collection is completed. In an embodiment, all components of the device 100 are part of an integrated unit, meaning that all components are connected to form a unit. An integrated device 100 minimizes the likelihood of a part not being accounted for because that part is used in performing the test or because it would be obvious to the sample collector that the part was missing from the integrated unit.

Inappropriate materials and practices used for sample collection and sample processing can cause false negative results where the presence of a pathogenic organism is missed. This could lead to a false conclusion that the manufacturing area is safe for production. In an embodiment, the device 100 enhances sample collection by assisting the analyst in the collection of a representative sample. The device 100 can enhance the ability of the analyst to firmly press down onto a sampling surface. The device 100 can also improve the ability of the analyst to collect a surface sample with minimal opportunity for accidental contamination. In an embodiment, the device 100 permits the use of collection sponges that facilitate vigorous scrubbing of larger surfaces without the need for the analyst's hand to be in contact with the sampling sponge or even near the sampling sponge to avoid accidently contamination from the hand. In an embodiment, the device 100 allows the analyst to initiate enrichment of the sample at the point of collection, avoiding the need to further manipulate the sampling device by adding enrichment broth once the sampling device is received in the laboratory. For example, a sponge sample is typically received in a laboratory in a flexible sample bag with a wire closure mechanism. Enrichment broth needs to be added to the sample bag and this is done by the analyst unrolling the wire closure, opening the sample bag by pulling tabs on the outside of the bag that are attached to the wire closure, pouring in a fixed amount of enrichment broth, and reclosing the sample bag by rolling down the bag and securing by bending over the wire closure. This manipulation to add in enrichment broth is a time consuming and inefficient process that elevates the possibility of accidental introduction of microbial contaminants into the sample.

In an embodiment, the device 100 allows the analyst to (i) collect a surface sample using a collection sponge hydrated with a non-toxic collection solution, (ii) initiate sample processing immediately or soon after the sample has been collected by introducing the microorganisms collected on the sponge to an enrichment broth present in the sampling device, and (iii) access the enrichment broth contained in the device easily and safely for further analyses, such as running a diagnostic test for detection of the target microorganism in the enrichment broth.

As compared to the device described in U.S. Pat. No. 9,027,420 B1, the device 100 of the present invention provides for the opportunity by the user to more aggressively scrub a surface when sampling to disrupt biofilms on the surface and dislodge strongly attached microorganisms. Unlike the device of U.S. Pat. No. 9,027,420 B1, the current device 100 avoids the use of a swab with a shaft and instead utilizes a sponge attached to a rigid flat surface of the cap. The problem with a sampling device that uses a shaft with a sponge or fibers attached to the tip of the shaft is that the shaft reduces the user's ability to apply maximum pressure to the sponge during surface scrubbing, as the shaft bends under pressure. A further advantage of the present device 100 of the invention over the device of U.S. Pat. No. 9,027,420 B1 is that an access port is incorporated into the device 100 that permits the user to easily, safely and aseptically remove an enriched sample for processing with a diagnostic test. The device of U.S. Pat. No. 9,027,420 B1 does not contain such an access port for collecting an aliquot of enriched sample for testing, which increases the possibility that a laboratory worker could be exposed to pathogenic microorganisms upon removal of the enrichment broth for testing. The device 100 of the present invention is easily scalable in terms of the size of sponge used with the device so that a manufacturer could provide devices of different dimensions to permit the user to test larger surface areas. Finally, the device 100 of the present invention is stackable to facilitate the transport of the device back to the laboratory and the handling of the device in the laboratory. With references to the FIGURES, an embodiment of the sampling device 100 will be described.

FIG. 1 illustrates an embodiment of the sampling device 100 with a cutaway section to show the internal constructions. In FIG. 1, from top to bottom, the device 100 includes a lid 104, a cap 102, and a bowl 106, all three being removably coupled into a single device 100. The device 100 allows for disassembly of the lid 104 from the cap 102 to collect a sample. Then, the cap 102 and bowl 106 are disassembled and reassembled in a different orientation for enrichment of the sample. Finally, the lid 104 can be reassembled to the cap 102 on the side of the cap 102 that was previously attached to the bowl 106. The lid 104 generally has a cylindrical sidewall with two ends. One end of the lid 104 is open, while the opposite end is closed. Similarly, the bowl 106 can be described as having a cylindrical sidewall with two ends, with one open end and a closed end. In addition to holding the collection sponge, the cap 102 functions to close the open end of the bowl 106.

The cap 102 has a collection sponge 112 attached or glued on a raised flat platform 122 of the cap 102. In an embodiment, a small amount of hot melt glue or other non-toxic adhesive can be used to firmly secure the collection sponge 112 in position.

The collection sponge 112 can be made of any known absorbent, porous, natural, or synthetic material. The collection sponge 112 can be pliable or rigid. Further, the collection sponge 112 can include one of a sponge, a foam, woven fabrics, or non-woven fabrics. In an embodiment, the collection sponge 112 is a dense sponge that will withstand vigorous scrubbing without damage or shedding, such as polyurethane foam. In an embodiment, the collection sponge 112 is disk-shaped to define a generally flat circular shape that has a diameter greater than the height of the collection sponge 112. In other embodiments, the collection sponge 112 may have a different shape than illustration, for example, the collection sponge 112 can be oval, rectangle, or have any number of straight sides such as, pentagon, hexagon, etc.

In an embodiment, to allow for collection of samples over large surface areas, the collection sponge 112 has a diameter that is at least equal to or greater than the height. That is, the aspect ratio of diameter to height of the collection sponge 112 is 1 or greater. An aspect ratio greater than 1 signifies that the diameter of the collection sponge 112 is greater than its height. Further, the aspect ratios of the lid 104, the cap 102, and the bowl 106 can also be 1 or greater. That is, the diameter of the lid 104, the cap 102, and the bowl 106 can be greater than the height.

In an embodiment, the collection sponge 112 diameter can be about 3 inches. In an embodiment, the collection sponge 112 diameter can be greater than 3 inches. In an embodiment, the collection sponge 112 diameter can be less than 3 inches, for example, 2 or even 1 inch or any diameter from 1 inch or greater. Devices 100 can be manufactured having various diameter collection sponges 112 or various collection sponge 112 shapes for use in different applications. For example, the sponge 112 can have an oval or rectangular shape. A collection sponge 112 with a large surface area allows the sampling of correspondingly larger areas as well.

In an embodiment, the sponge 112 is hydrated with collection solutions such as HiCap™ Neutralizing Broth, a proprietary broth by World Bioproducts of Woodinville, Wash., a neutralization solution called neutralizing Buffered Peptone Water, formulated by researchers at the United States Department of Agriculture, or traditional collection solutions such as D/E neutralizing broth (Neogen, Lansing, Mich.), letheen broth (Neogen, Lansing, Mich.), or neutralizing buffer (BD, Cockeysville, Md.). A suitable amount of collection solution added to the sponge is about 10 milliliters. However, other embodiments can have more or less than 10 milliliters. The device 100 can be preloaded with collection solution at the time of manufacture, or the user can load the sponge 112 with whatever collection solution is appropriate for the particular surface to be sampled or test to be conducted. A watertight seal to the lid 104 prevents leakage and also protects and maintains sterility of the collection sponge 112 prior to use.

Figure 2:
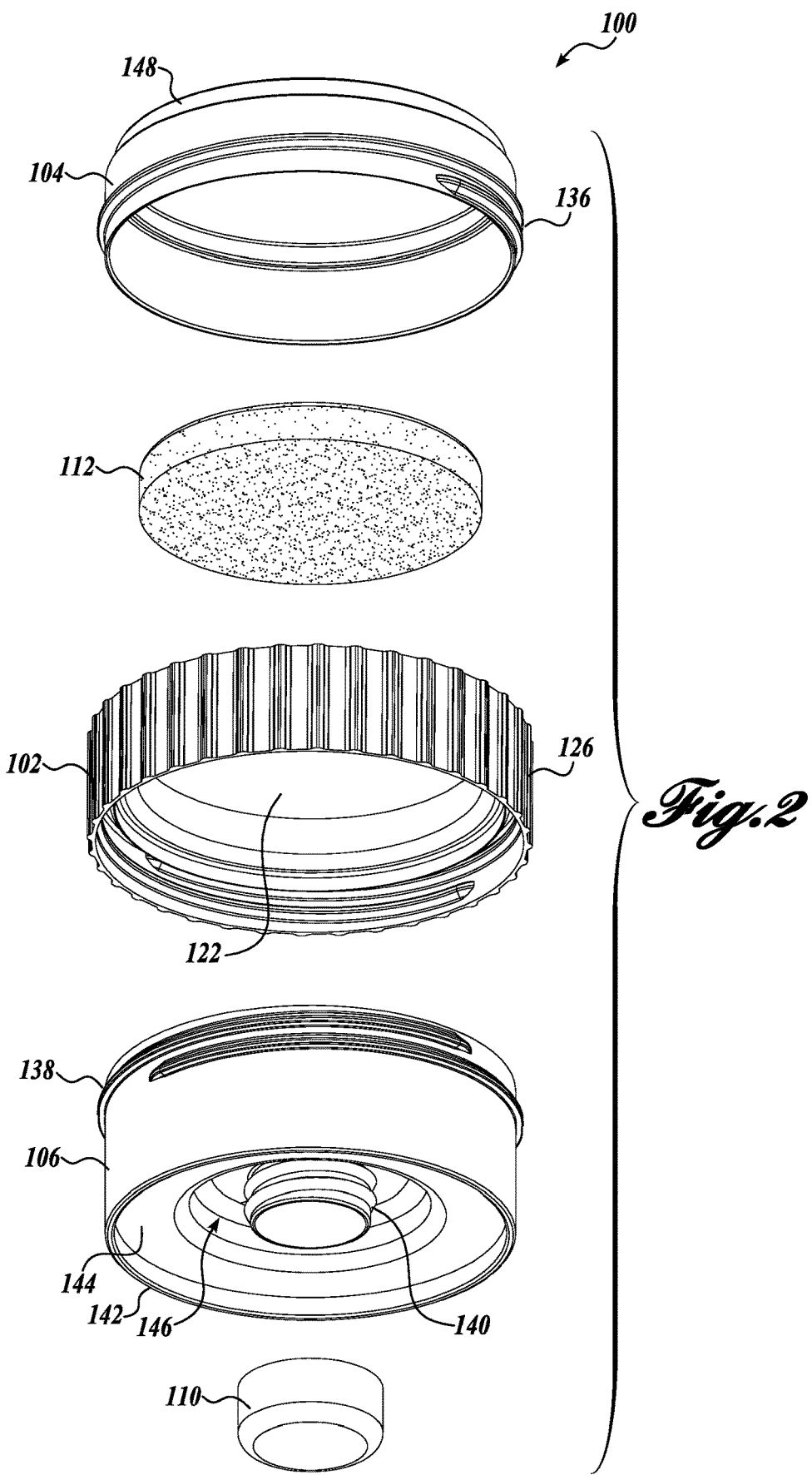
FIG. 2 is a diagrammatical illustration of an embodiment of the sampling device of FIG. 1 showing the major components.

Referring to FIG. 2, the device 100 components are separated to more clearly understand the construction. The cap 102 has two ends closed off and separated by each other by the round platform flat piece 122. The exterior circumference or grip band 126 of the cap 102 can be provided with alternating grooves and ridges to increase the ability to grip and twist the cap 102 on and off the bowl 106. From FIG. 1, the round platform piece 112 is attached to the inside of the exterior band 126 via a horizontal circular edge 128 or "shelf" to separate the cap 102 into a first (upper) and second (lower) end closed off from each other. The raised platform piece 122 is formed by connecting a circular sidewall to the horizontal edge 128, and then closing the end of the circular sidewall with a flat piece. Thus, one side has the raised platform 122 and the other side has a cup-shaped form. A first circular lip 132 low in height extends perpendicular and above the horizontal edge 128. A second circular lip 134 low in height extends perpendicular to and below the horizontal edge 128. Although circular lips 132 and 134 are shown, other embodiments of the cap 102 may exclude the lips and simply have a flat surface for mounting the collection sponge 112.

Still referring to FIG. 1, the inside surface of the grip band 126 is provided with inner screw threads 116 above the horizontal edge 128 and with inner screw threads 114 below the horizontal edge 128. A first U-shaped channel is formed from the inner surface screw threads 116 and the circular lip 132. A second U-shaped channel is formed from the inner surface screw threads 114 and the circular lip 134. The first and second U-shaped channels are configured to receive the open-ended circular edges of both the lid 104 and bowl 106. Accordingly, the cap 102 is threadable to, or otherwise connectable, to the bowl 106 on one end. The cap 102 is threadable to, or otherwise connectable, to the bowl 106 on the opposite end.

In FIG. 2, the open ended circular edge of the lid 104 has outer threads 136, and the open ended circular edge of the bowl 106 has outer threads 138. The outer threads 136 of the lid 104 are configured to thread into both inner threads 116 and 114 of the cap 102. Thus, the lid 104 can be attached and removed from both ends of the cap 102. The outer threads 138 of the bowl 106 are configured to thread into both inner threads 116 and 114 of the cap 102. Thus, the bowl 106 can be attached and removed from both ends of the cap 102.

Although the cap 102, lid 104, and bowl 106 are shown with threads in one embodiment, other embodiments may use alternative connecting means, such as pressure fitted parts or snap together parts. The cap 102 forms a watertight seal to the bowl 106 when connected at either end. Additional gaskets (not shown) may be provided between the cap 102 and bowl 106 connection to ensure water tightness. The cap 102 forms a watertight seal to the lid 104 at either end. Additional gaskets (not shown) may be provided between the cap 102 and lid 104 connection to ensure water tightness.

While the illustrated embodiment shows that the cap 102 has internal threads on both ends, other embodiments of the cap 102 can have external threads on both ends. Also, the illustrated embodiment shows that the lid 104 and bowl 106 each has external threads, however, other embodiments of the lid 104 and bowl 106 can both have internal threads when the cap 102 has external threads.

Referring to FIG. 2, the bowl 106 includes a sampling port 140 on the closed end of the bowl 106. The sampling port 140 may include threads to secure a sampling port plug 110 thereto. In an embodiment, the sampling port 140 is recessed into the bowl 106 so that the sampling port 140 and plug 110 are at least flush with the bottom piece 144 of the bowl 106. As seen in FIG. 2 the recessed sampling port 140 creates an annular empty area 146 in the bowl 106. The annular space 146 allows removing and replacing the plug 110. The bowl 106 also includes a circular lip 142 extending down around the circumference of the closed end of the bowl 106. The circular lip 142 is used when stacking two or more devices 100 on top of each other. For this purpose, the lid 104 has a step section 148 at the closed end that is of smaller diameter than the remainder of the lid 104. Thus, the circular lip 142 of the bowl 106 from one device can fit over the step 148 of the lid 104 of a second device 100.

In FIG. 2, the collection sponge 112 is seen to be a disk shaped sponge and can be made to have a diameter that corresponds to the diameter of the raised platform piece 122.

In FIG. 1, the lid 104 is attached to the cap 102 so that the collection sponge 112 is covered by the lid 104, and the bowl 106 is attached to the cap 102 at the opposite end. As mentioned herein, the collection sponge 112 can be pre-wetted with a collection solution or broth, and the bowl 106 can contain an enrichment solution or broth. Thus, with the collection and enrichment broths provided, the device 100 of FIG. 1 is ready to be used to collect a sample from a large surface area.

Before using the device 100 of FIG. 1 to collect a sample, the collection sponge 112 is covered by the lid 104, and the bowl 106 is attached to the cap 102 on the end opposite to the collection sponge 112. When finished collecting a sample, the bowl 106 is disconnected from the cap 102 and re-attached to the end of the cap 102 with the collection sponge 112 to expose the collection sponge 112 to the enrichment broth in the bowl 106. Further, the lid 104 can then be attached to the side of the cap 102 that is not connected to the bowl 106.

Figure 3:
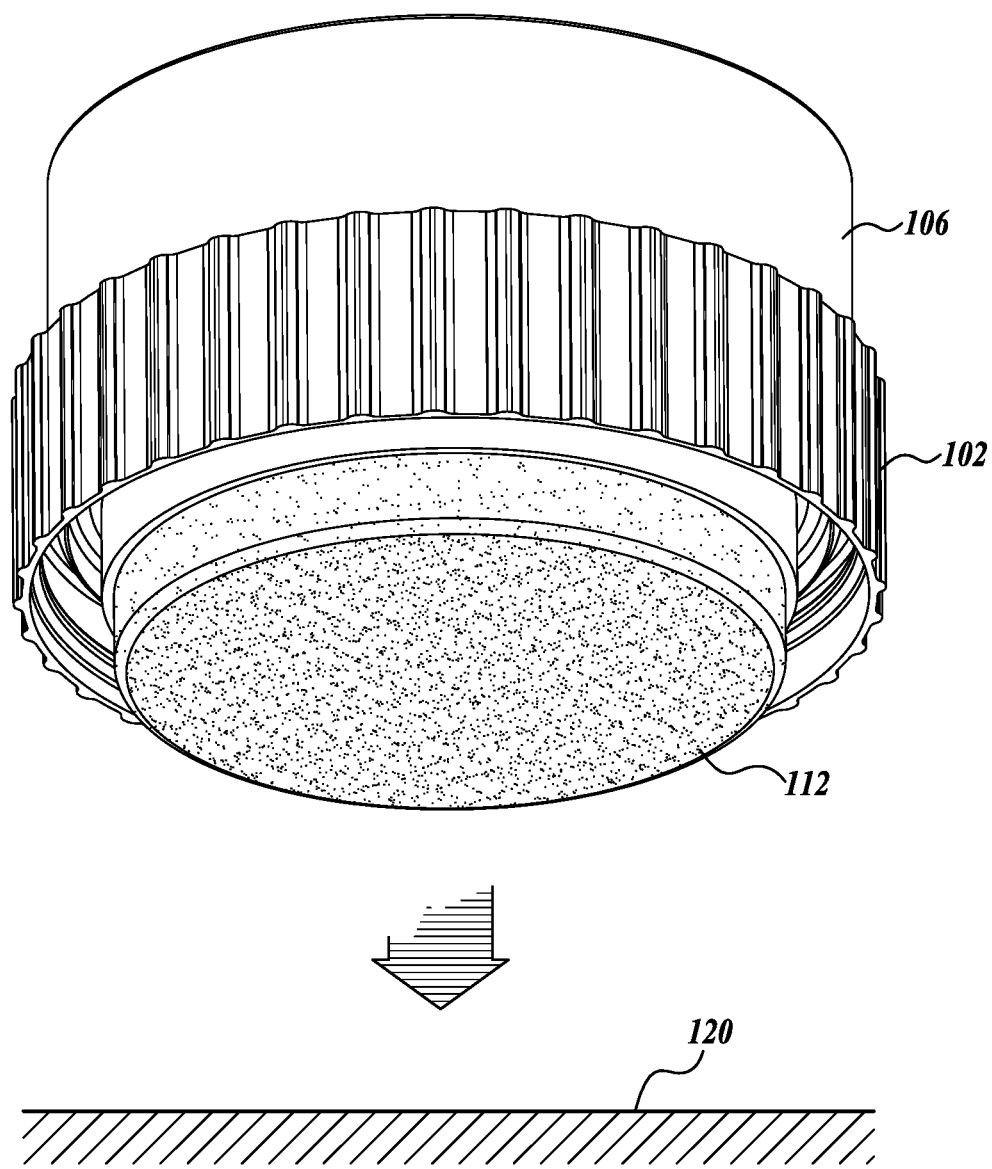
FIG. 3 is a diagrammatical illustration of an embodiment of a bowl and cap of the sampling device of FIG. 1, after removing the lid and inverting the bowl and cap to collect a sample.
Figure 4:
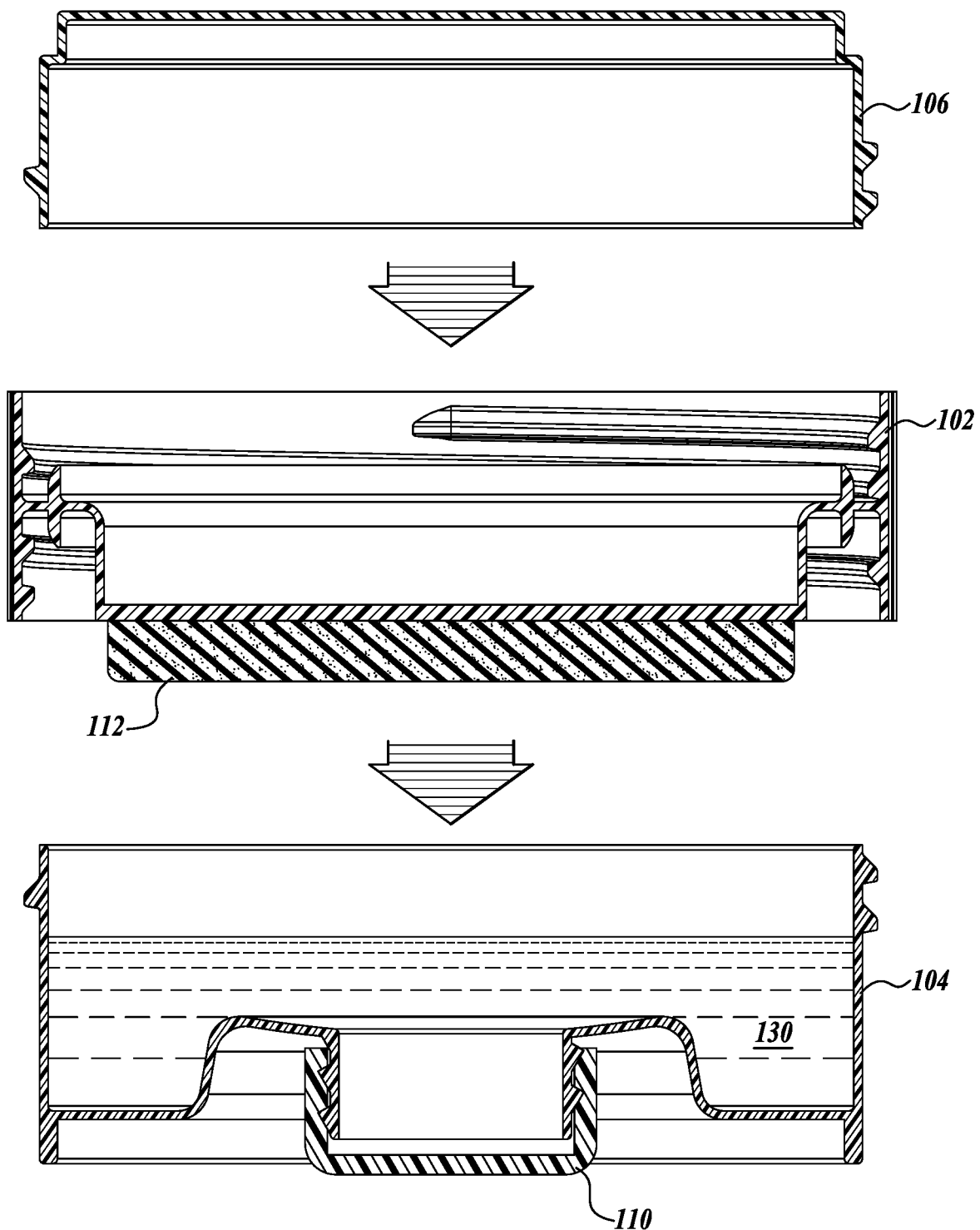
FIG. 4 is a diagrammatical illustration of an embodiment of the sampling device of FIG. 1 after collecting a sample, bowl is removed from the cap and re-attached so that the sponge is inside the bowl, lid is re-attached to the side of the cap that was previously attached to the bowl.
Figure 5:
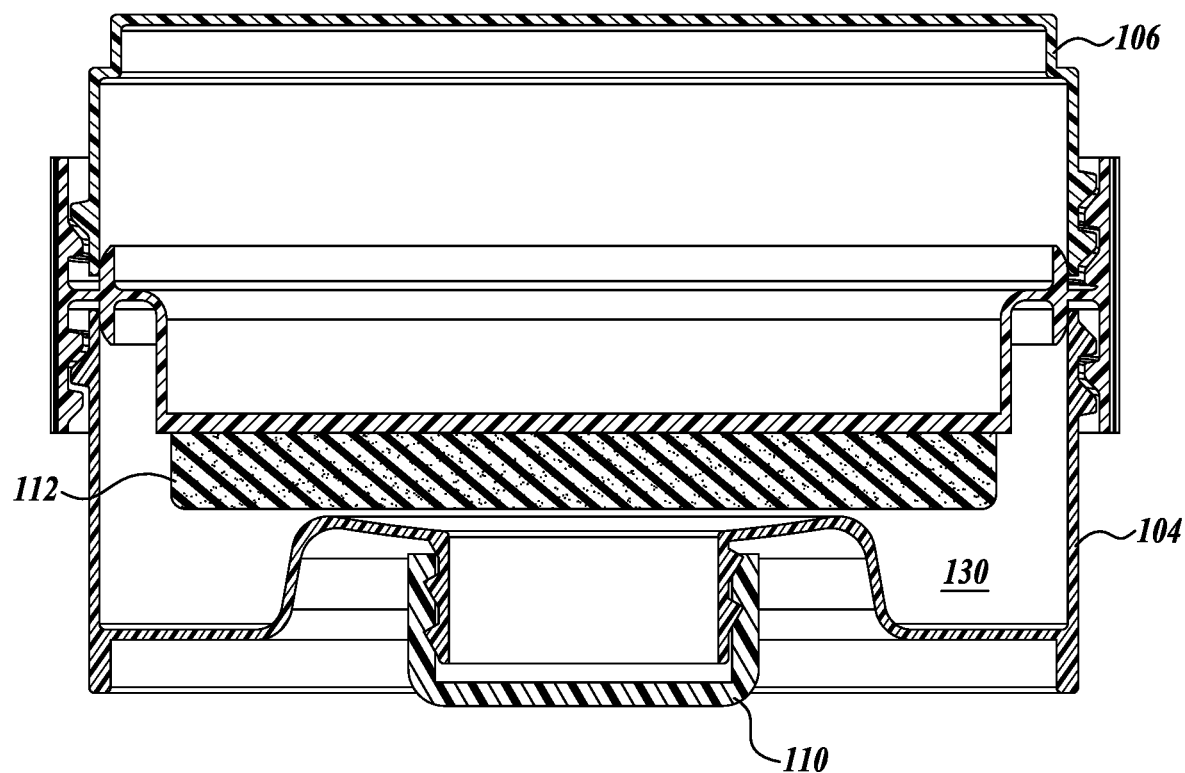
FIG. 5 is a diagrammatical illustration of an embodiment of the sampling device of FIG. 1 after the cap is reattached to the bowl in the inverted position, and the lid is reattached to the cap.

As described, a feature of the cap 102, lid 104, and bowl 106 is that the cap 102 allows both the lid 104 and bowl 106 to attach to both ends of the cap 102. Thus, prior to use, the device 100 is assembled, such that the side of the cap 102 with the collection sponge 112 is attached to the lid 104, and the bowl 106 is attached to the opposite end of the cap 102. Thus, the collection sponge 112 is not exposed to the enrichment broth in the bowl 106, and the lid 104 protects the collection sponge 112. To collect a sample, the lid 104 is removed, while the bowl 106 can stay attached to the cap 102. The lid 104 can be set aside and is preferably not discarded. The collection sponge 112 with the bowl 106 attached can then be used to collect a sample from a surface as shown in FIG. 3. After the collection sponge 112 has been used to collect the sample, the bowl 106 is detached from the cap 102, and the side of the cap 102 with the collection sponge 112 can now attached to the bowl 106 so that the collection sponge 112 is exposed to the enrichment broth, which is illustrated in FIG. 4. The lid 104 can then be attached to the opposite end of the cap 102 (without the collection sponge 112), which is also illustrated in FIG. 4. The reassembled device 100 where the lid 104 is attached to where the bowl 106 used to be attached (FIG. 1), and the bowl 106 is attached to where the lid 104 used to be attached (FIG. 1) to once again provide an integrated device is shown in FIG. 5. Since the lid 104 and bowl 106 can attach to both ends of the cap 102, all of the components of the device 100 can be secured together so that nothing will inadvertently be left behind.

In one embodiment, the bowl 106 acts as a convenient grip to increase the gripping area when collecting a surface sample. Thus, one can apply greater pressure on the collection sponge 112 for aggressively scrubbing a surface to lift strongly attached microorganisms. Because device 100 is scalable to allow for the use of larger sponges, greater surface areas can be sampled efficiently and effectively, allowing the user to work with a sampling tool with an ergonomic advantage. Another benefit is spacing of the hand of the user away from the surface 120 being sampled and the surrounding environment to avoid physical contact with the hand of the user that could cause contamination.

In an embodiment, the bowl 106 can be loaded with a desired enrichment broth 130, for example, UVM Broth or Demi-Fraser Broth for *Listeria* detection or Buffered Peptone Water for *E. coli* or *Salmonella* detection (see Table 1 for additional examples of enrichment broths). A suitable amount of enrichment broth 130 in the bowl is about 90 milliliters. However, other embodiments can have more or less than 90 milliliters. The device 100 can be preloaded with enrichment broth 130 at the time of manufacture, or the user can load the bowl 106 with whatever enrichment broth is appropriate for the particular test to be conducted.

Referring to FIG. 5, another aspect of the device 100 is the provision for a sampling port 140 and plug 110 provided on the closed side of the bowl 106. The sampling port 110 allows access to the enrichment broth 130 after the collection sponge 112 has been exposed to the enrichment broth 130. The plug 110 allows opening and closing the sampling port 140. Via the sampling port 140, one may safely and easily remove an aliquot for testing with a standard culture method as described in the Compendium of Methods for the Microbiological Examination of Food or with an advanced diagnostic method based upon molecular amplification technology such as PCR or an antibody based technology such as an immunoassay. In an embodiment, the sampling port 140 and plug 110 do not project beyond the lower edge of the bowl 106 to prevent interference when stacking multiple devices 100.

In addition to a device 100, a method is also disclosed for taking a sample. The method includes removing the lid 104 from the device, thereby, exposing the collection sponge 112, then inverting the device 100 so that collection sponge 112 faces the surface 120 to be sampled, as seen in FIG. 3. In an embodiment, the bowl 106 remains attached to the cap 102 during sampling, and the cap 102 acts as a lid to prevent spillage from the bowl 106. The bowl 106 and cap 102 allow a firm grip for applying pressure with the collection sponge 112 to a large surface area, for example.

Next, when the scrubbing of the surface is completed, the bowl 106 is uncoupled from the cap 102, and the cap 102 is coupled to the bowl 106 so that that collection sponge 112 is exposed to the enrichment broth 130, as seen in FIGS. 4 and 5. This leaves the opposite end of the cap 102 available for coupling to the lid 104, also seen in FIGS. 4 and 5. In this way, the enrichment broth 130 is applied to the sample collected by the collection sponge 112 without delay, despite the fact that different collection and enrichment solutions/broths are used. The assembled device after taking a sample is shown in FIG. 5. The amount of enrichment broth in the bowl 106 is sufficient so that the collection sponge 112 contacts the broth 130. The device 100 may be turned so that the device rests on the lid 104. In this inverted position, the sampling port 140 is accessible at the top and an aliquot may be removed from the bowl 106.

Representative embodiments include a sampling device 100 comprising a cap 102 having two ends and a collection sponge 112 attached on one end, wherein a collection sponge diameter is greater than a collection sponge height; a lid 104 removably attached to a first end of the cap 102 to cover the collection sponge 112; and a bowl 106 removably attached to a second and opposite end of the cap 102, wherein the bowl 106 contains an enrichment broth 130.

In an embodiment of the sampling device 100, the cap 102 has a solid piece 122 between the first and second ends that closes the first end from the second end and seals the bowl 106.

In an embodiment of the sampling device 100, the solid piece is a raised platform 122 and the collection sponge 112 is attached to the raised platform.

In an embodiment of the sampling device 100, the lid 104 has a cylinder shaped sidewall, an open end, and a closed end, wherein the open end is attached to the cap 102.

In an embodiment of the sampling device 100, the bowl 106 has a cylinder shaped sidewall, an open end, and a closed end, wherein the open end is attached to the cap 102 on an opposite side from the lid.

In an embodiment of the sampling device 100, the lid 104 is attached to the cap 102 via threads, and the bowl 106 is attached to the cap 102 via threads, wherein the threads of the lid 104 are similar to the threads of the bowl 106.

In an embodiment of the sampling device 100, the lid 104 is attached to the cap 102 via threads, and the bowl 106 is attached to the cap 102 via threads, and the lid 104 can be threaded to the second end of the cap 102, and the bowl 106 can be threaded to the first end of the cap 102.

In an embodiment of the sampling device 100, the cap 102 has a solid piece between the first and second ends that closes the first end from the second end to close off the bowl 106 from the lid 104.

In an embodiment of the sampling device 100, the sampling device 100 further comprises a lip 142 extending from a closed end of the bowl 106.

In an embodiment of the sampling device 100, the lid 104 has a closed end and an open end, and the open end has threads.

In an embodiment of the sampling device 100, the bowl 106 has a closed end and an open end, and the open end has threads.

In an embodiment of the sampling device 100, the bowl 106 has a closed end and an open end, and the closed end has a sampling port 140 and plug 110.

In an embodiment of the sampling device 100, the cap 102 has a cap diameter greater than a cap height.

In an embodiment of the sampling device 100, the lid 104 has a lid diameter greater than a lid height.

In an embodiment of the sampling device 100, the bowl 106 has a bowl diameter greater than a bowl height.

An embodiment of a method of sampling a surface comprises scrubbing a surface with a collection sponge 112 having a collection sponge diameter greater than a collection sponge height, wherein the collection sponge 112 is attached to a first end of a cap 102, and a second end of the cap is removably attached to a bowl 106 containing an enrichment broth 130; and detaching the bowl 106 from the second end of the cap 102 and attaching the first end of the cap 102 to the bowl 106, wherein the collection sponge 112 is exposed to the enrichment broth 130 in the bowl 106.

In an embodiment of the method, the method further comprises detaching a lid 104 covering the collection sponge 112 from the first end of the cap 102 before the collection sponge 112 is used to collect a sample.

In an embodiment of the method, the method further comprises attaching the lid 104 to the second end of the cap 102 after the bowl 106 is detached.

In an embodiment of the method, the method further comprises taking a sample of the enrichment broth 130 through a closed end of the bowl 106.

In an embodiment of the method, the method further comprises selecting an enrichment broth 130 and adding the enrichment broth 130 to the bowl 106 before taking a sample with the collection sponge 112.

A method for taking a sample and culturing the sample, comprising scrubbing a surface with a collection sponge 112 having a collection broth and picking up a microorganism on the collection sponge 112, wherein the collection sponge 112 is attached to a first end of a cap 102, and a second end of the cap 102 is removably attached to a bowl 106 containing an enrichment broth 130, detaching the bowl 106 from the second end of the cap 102 and attaching the first end of the cap 102 to the bowl 106, wherein the collection sponge 112 and microorganism is exposed to the enrichment broth 130 in the bowl 106, and incubating at least the bowl 106 and cap 102 with the microorganism exposed to the enrichment broth 130.

While illustrative embodiments have been illustrated and described, it will be appreciated that various changes can be made therein without departing from the spirit and scope of the invention.

The invention claimed is:

1. A sampling device, comprising:
   a cap having a first open end and a second open end and a collection sponge attached on one end, wherein a collection sponge diameter is greater than a collection sponge height;
   a lid removably attached to the first end of the cap to cover the collection sponge; and
   a bowl removably attached to the second and opposite end of the cap, wherein the bowl contains an enrichment broth, wherein the cap has an exterior band and a solid piece is attached inside of the band between the first and second open ends, wherein the first open end is closed off from the second open end, and the bowl is closed off from the lid.

2. The sampling device of claim 1, wherein the solid piece includes a raised platform that is attached via a horizontal edge to the inside of the band, and the horizontal edge is attached to a sidewall to which the raised platform is attached, and the collection sponge is attached to the raised platform.

3. The sampling device of claim 1, wherein the lid has a cylinder shaped sidewall, an open end, and a closed end, wherein the open end is attached to the cap.

4. The sampling device of claim 1, wherein the bowl has a cylinder shaped sidewall, an open end, and a closed end, wherein the open end is attached to the cap on an opposite side from the lid.

5. The sampling device of claim 1, wherein the lid is attached to the cap via threads, and the bowl is attached to the cap via threads, wherein the threads of the lid are similar to the threads of the bowl.

6. The sampling device of claim 1, wherein the lid is attached to the cap via threads, and the bowl is attached to the cap via threads, and the lid can be threaded to the second end of the cap, and the bowl can be threaded to the first end of the cap.

7. The sampling device of claim 1, further comprising a lip extending outward from and around a periphery of a closed end of the bowl.

8. The sampling device of claim 1, wherein the lid has a closed end and an open end, and the open end has threads.

9. The sampling device of claim 1, wherein the bowl has a closed end and an open end, and the open end has threads.

10. The sampling device of claim 1, wherein the bowl has a closed end and an open end, and the closed end has a sampling port.

11. The sampling device of claim 1, wherein the cap has a cap diameter greater than a cap height.

12. The sampling device of claim 1, wherein the lid has a lid diameter greater than a lid height.

13. The sampling device of claim 1, wherein the bowl has a bowl diameter greater than a bowl height.

14. The sampling device of claim 1, wherein the collection sponge is a polyurethane foam sponge.

15. A method of sampling a surface, comprising:
   providing a sampling device of claim 1;
   scrubbing a surface with the collection sponge having the collection sponge diameter greater than the collection sponge height, wherein the collection sponge is attached to the first end of the cap, and the second end of the cap is removably attached to the bowl containing the enrichment broth; and detaching the bowl from the second end of the cap and attaching the first end of the cap to the bowl, wherein the collection sponge is exposed to the enrichment broth in the bowl.

16. The method of claim 15, further comprising detaching the lid covering the collection sponge from the first end of the cap before the collection sponge is used to collect a sample.

17. The method of claim 16, further comprising attaching the lid to the second end of the cap after the bowl is detached.

18. The method of claim 17, further comprising taking a sample of the enrichment broth through a closed end of the bowl.

19. The method of claim 15, further comprising selecting an enrichment broth and adding the enrichment broth to the bowl before taking a sample.

20. A method for taking a sample and culturing the sample, comprising:

providing a sampling device of claim 1;

scrubbing a surface with the collection sponge having a collection broth and picking up a microorganism on the collection sponge, wherein the collection sponge is attached to the first end of the cap, and the second end of the cap is removably attached to the bowl containing the enrichment broth;

detaching the bowl from the second end of the cap and attaching the first end of the cap to the bowl, wherein the collection sponge and microorganism are exposed to the enrichment broth in the bowl; and incubating at least the bowl and cap with the microorganism exposed to the enrichment broth.

* * * * *